United States Patent [19]

Friedman

[11] 4,271,841
[45] Jun. 9, 1981

[54] ELECTRO-OCULAR STIMULATION SYSTEM

[75] Inventor: Harry G. Friedman, Plymouth, Minn.

[73] Assignee: Medtronic, Inc., Minneapolis, Minn.

[21] Appl. No.: 117,061

[22] Filed: Jan. 31, 1980

[51] Int. Cl.³ ............................................. A61N 1/36
[52] U.S. Cl. ................................. 128/419 R; 128/793
[58] Field of Search ................ 128/419 R, 421, 422, 128/791, 793, 784

[56] References Cited

U.S. PATENT DOCUMENTS

| | | | |
|---|---|---|---|
| 2,525,381 | 10/1950 | Tower | 128/793 |
| 3,727,616 | 4/1973 | Lenzkes | 128/422 |

*Primary Examiner*—William E. Kamm
*Attorney, Agent, or Firm*—Schroeder, Siegfried, Ryan, Vidas, Steffey & Arrett

[57] ABSTRACT

A system for the treatment of ocular misalignment by electrical stimulation of ocular recti. A body implantable unit develops an electrical stimulation signal and delivers that signal to an ocular rectus without restricting its contraction. In a preferred embodiment, the implanted unit includes a receiving member which cooperates with an external transmitting unit, the external transmitting unit establishing the stimulation signal parameters. Preferably, the stimulation signal is a periodically interrupted train of pulses, the repetition rate of the stimulation signal pulses being within the range of 50 to 100 pulses per minute. The interruption of the pulse train results in a stochastic stimulation with the pulse train being delivered for approximately 1 to 5 seconds with the interval between stimulation signals being from approximately 5 to 25 seconds. The pulse amplitude may be selectively established in the range from about 0.8 to 15 volts with the pulses having a pulse width of approximately 0.22 milliseconds. During stimulation, a divergence movement is attained to correct the ocular misalignment while chronic stimulation results in a histological and anatomical change in the stimulated rectus which also tends to overcome the ocular misalignment.

12 Claims, 4 Drawing Figures

ELECTRO-OCULAR STIMULATION SYSTEM

DESCRIPTION

Background of Prior Art

Conjugate movement of the eyes is necessary for many visual processes. Eye movement is controlled by three separate muscle pairs, the muscles of each pair operating reciprocally to effect eye movement. An imbalance within any of the ocular muscle pairs results in an ocular misalignment or strabismus.

Strabismus is present in about two percent of the population. Not only is it cosmetically disfiguring but also frequently results in a loss of functional binocular vision (amblyopia). It is most common in the first five years of life and if not treated early enough one eye may become physiologically blind.

The presently accepted treatment for strabismus is a surgical procedure in which both muscles of the imbalanced muscle pair are cut with one being shortened and the other being lengthened. It is often necessary to repeat this procedure a second and a third time. Also, it has been reported that some binocular cooperation following surgical correction occurs in only 33 percent of infants on which the procedure is performed. Further, while surgery alters the anatomic and mechanical parameters of the eye muscles, it does not affect the abnormal tonus input.

BRIEF SUMMARY OF THE INVENTION

The present invention has application to the treatment of infantile idiopathic strabismus, paralytic strabismus, nerve palsy, wandering eye and other similar ocular misalignments and recognizes that the eye muscles or recti have low fatigue and that the time to fatigue can be increased with exercise. The ocular misalignment is treated by electrical stimulation of the ocular recti and, particularly, the agonistic muscle of an ocular muscular pair. Not only does stimulation of the agonistic muscle tend to overcome the stronger antagonistic muscle but a central nervous system reflex has a tendency to relax the antagonistic muscle to further aid the agonistic.

A body implantable unit develops an electrical stimulation signal and delivers the same to the ocular rectus to be stimulated without restricting or interferring with its contraction. Stimulation may be delivered via an electrode which rests on the muscle or is affixed to it in a manner which allows it to contract. In a preferred embodiment, the implantable unit includes a receiving portion which cooperates with an external transmitting unit, the external unit establishing the parameters of the stimulation signal. To provide a smooth muscle contraction, the stimulation signal is a pulse train of relatively high repetition rate, preferably within the range of 50–100 pulses per minute. For the comfort of the patient, as well as to reduce muscle fatigue the stimulation signal may be stochastic as by periodically interrupting the train of pulses. In a preferred embodiment, the stimulation signal occurs for a period of from approximately 1 to 5 seconds and is interrupted for an interval of from approximately 5 to 25 seconds. Pulse amplitude is established within the range from about 0.8 to 15 volts and is typically on the order of 2 volts. A desirable pulse width is approximately 0.22 milliseconds.

Stimulation of the type described will overcome an imbalance in the reciprocally acting ocular recti pairs to overcome an ocular misalignment. Chronic stimulation will result in a histological and anatomical change (hyterprophy) to assist the agonistic muscle in overcoming its imbalance relative to the antagonistic muscle, without continued stimulation. After sufficient correction is attained, the implantable unit may be left in place for later use, if necessary. In chronic applications, it may be desirable to implant a self-contained pulse generating unit.

DETAILED DESCRIPTION OF THE DRAWINGS

Figure 1:
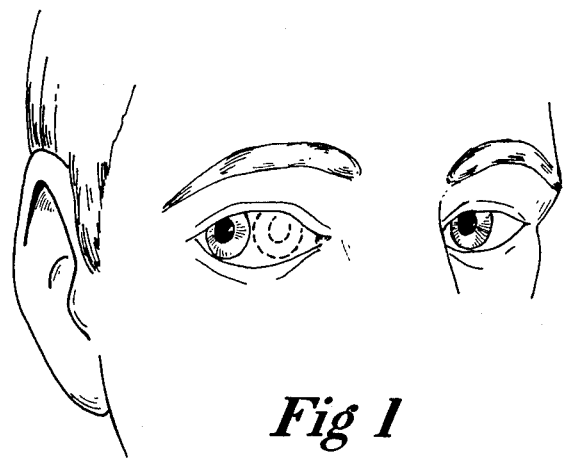
FIG. 1 is a partial front facial view illustrating an ocular misalignment to which the present invention is directed.

FIG. 1 illustrates a partial front facial view in which normal conjugate movement of the eyes has positioned them to view toward the right (to the observer's left when viewing the Figure). In the event of an imbalance between lateral and medial rectus in the right eye, with the medial rectus being the antagonistic muscle and the lateral rectus being the agonistic muscle, that eye will be pulled to the left (to the observer's right) as shown in phantom in FIG. 1. This is a type of ocular misalignment to which the present invention is directed.

Figure 2:
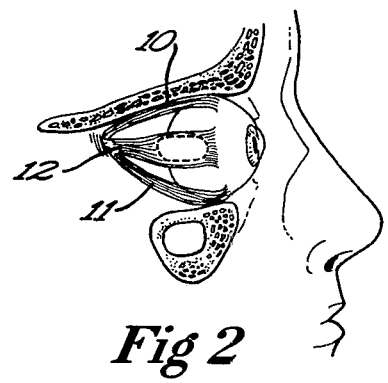
FIG. 2 illustrates a desired electrode placement area on an agonistic ocular rectus (the lateral rectus) to overcome an imbalance between it and its antagonistic ocular rectus (the medial rectus).

Referring now to FIG. 2, there is illustrated a side view of the right eye including the reciprocally acting superior and inferior recti 10 and 11, respectively, and the lateral rectus 12. In the misalignment illustrated in phantom in FIG. 1, the antagonistic medial rectus (not shown) is overpowering the agonistic lateral rectus 12. Stimulation delivered to the lateral rectus 12, without restricting or interferring with its contraction, will assist agonistic lateral rectus 12 in overcoming the antagonistic medial rectus. Further, such stimulation results in a central nervous system reflex that relaxes the antagonistic medial rectus to aid the agonistic lateral rectus 12. An electrode overlying the region 13 on the lateral rectus 12 will result in the desired contraction of the rectus 12 on the delivery of appropriate stimulation energy. The electrode may overlie the region 13 and rest thereon so as to not interfere with or restrict the contraction of the rectus 12. Alternatively, the electrode may be affixed to the rectus 12 so long as the manner of fixation does not restrict or interfere with its contraction. A series of contacts carried by a lead may be employed to provide a non-rigid structure which may be affixed to the rectus while allowing its contraction.

In a preferred embodiment, an implantable unit is formed of a receiving member responsive to transmitted radio frequency signals to develop a stimulation signal and a lead and associated electrodes for delivery of the stimulation energy to the desired stimulation site. Alternatively, the implantable unit may be a self-contained signal generating unit. An example of a body implantable unit which is easily adapted to the present invention is disclosed in U.S. Pat. application Ser. No. 080,539 filed Oct. 1, 1979, in the name of Harry G. Friedman for BODY IMPLANTABLE ELECTRODE, which is commonly owned with the present invention and which is hereby incorporated by reference. As noted above, the implantable unit may be a radio frequency receiving unit, or, alternatively, may be a self-contained pulse generating unit. In either case, the implantable unit develops (under the control of an external transmitting unit in the case of an implanted receiving unit) a stimulation signal and delivers the same to a desired stimulation site via an associated electrode pair. As disclosed in the incorporated specification, the indifferent electrode may be carried by the housing of the implantable unit. Other implantable units may also be easily adapted to the system of the present invention.

Figure 3:
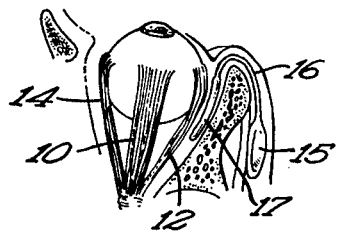
FIG. 3 illustrates the position of an implantable unit which develops and delivers a stimulation signal to the location illustrated in FIG. 2.
Figure 4:
FIG. 4 illustrates the placement of a portion of an external transmitting unit which cooperates with an implanted unit positioned as illustrated in FIG. 3.

FIG. 3 illustrates a top view of the eye of FIG. 2 including superior rectus 10, lateral rectus 12 and medial rectus 14 with a body implantable unit positioned for stimulation of the lateral rectus 12. The implantable unit contains a stimulation signal developing portion 15 which may be either of the radio frequency signal receiving type or a self-contained pulse generating unit. A lead 16 extends from the portion 15 and carries an electrode 17, the electrode 17 overlying the portion 13 of the lateral rectus 12 illustrated in FIG. 2. Electrode 17 may rest on the portion 13 or be affixed to the lateral rectus 12, as noted above, within the constraint that it not restrict or interfere with the contraction of the rectus 12. The stimulation signal developed by the portion 15 is preferably a pulse train of relatively high repetition rate to provide a smooth muscular contraction and, more preferably, is stochastic in nature for the comfort of the patient and to reduce muscle fatigue. The pulse repetition rate may be in the range of 50 to 100 pulses per minute with the signal being developed for a period of from approximately 1 to 5 seconds with an interval between signal development of approximately 5 to 25 seconds in duration. The pulse amplitude may be established within the range from about 0.8 to 15 volts. Typically, the pulse amplitude will be on the order of 2 volts and a pulse width of approximately 0.22 milliseconds has been found acceptable. Implantable receiving units and cooperating transmitting units as well as self-contained pulse generating units capable of operating within these parameters are within the knowledge of one of ordinary skill in the art. Alteration of the parameters within the ranges given is also within the knowledge of one of ordinary skill in the art. In most applications, it would be desirable to provide a unit in which the parameters are selectively alterable within the stated parameter ranges. The positioning of a transmitting antenna for cooperation within the implanted receiving unit, positioned as illustrated in FIG. 3 for stimulation of the right rectus, rectus is illustrated in FIG. 4.

Obviously, many modifications and variations of the present invention are possible in light of the above teachings. For example, while discussed in the context of stimulation of the lateral ocular rectus, the system of the present invention may be applied to any of the ocular recti without departing from the scope hereof. Also, as noted, the system of the present invention may be implemented by cooperating external and implanted transmitting and receiving units, respectively, or by a self-contained pulse generating unit. It is therefore to be understood that, within the scope of the appended claims, the invention may be practiced otherwise than as specifically described.

I claim:

1. A system for the treatment of ocular misalignment by electrical stimulation of ocular recti which comprises body implantable means for developing an electrical stimulation signal and means for delivering said signal to an ocular rectus without restricting its contraction.

2. The system of claim 1 wherein said stimulation signal generating means comprises external transmitting means and implanted receiving means.

3. The system of claim 1 wherein said electrical stimulation signal comprises a periodically interrupted train of pulses.

4. The system of claim 3 wherein said stimulation signal developing means comprises means for selectively establishing the repetition rate of said stimulation signal within the range of 50 to 100 pulses per minute.

5. The system of claim 4 wherein said stimulation signal developing means comprises means for developing said signal for from approximately 1 to 5 seconds and interrupting said signal for from approximately 5 to 25 seconds.

6. The system of claim 5 wherein said stimulation signal developing means comprises means for establishing the pulse amplitude from about 0.8 to 15 volts.

7. The system of claim 6 wherein the stimulation signal pulse width is approximately 0.22 milliseconds.

8. A system for inducing histological and anatomical change in an agonistic ocular rectus which comprises means for developing and delivering a stochastic train of stimulation pulses to said rectus.

9. The system of claim 8 wherein said stimulation pulses have a repetition rate within the range of 50 to 100 pulses per minute.

10. The system of claim 9 wherein said pulse train is delivered to said rectus for from approximately 1 to 5 seconds at intervals of approximately 5 to 25 seconds.

11. The system of claim 10 wherein said stimulation pulses have an amplitude from about 0.8 to 15 volts.

12. The system of claim 11 wherein said stimulation pulses have a pulse width of approximately 0.22 milliseconds.

* * * * *